United States Patent
Roy et al.

(10) Patent No.: US 10,774,058 B2
(45) Date of Patent: Sep. 15, 2020

(54) PROCESS FOR PREPARING D-GLUCARO-6,3-LACTONE

(71) Applicant: BASF SE, Ludwigshafen am Rhein (DE)

(72) Inventors: Abhijeet Roy, Navi Mumbai (IN); Dominik Ohlmann, Ludwigshafen (DE); Rahul Mulay, Navi Mumbai (IN); Priti Kulkarni, Navi Mumbai (IN); Vijay Narayanan Swaminathan, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/482,100

(22) PCT Filed: Feb. 7, 2018

(86) PCT No.: PCT/EP2018/053019
§ 371 (c)(1),
(2) Date: Jul. 30, 2019

(87) PCT Pub. No.: WO2018/146122
PCT Pub. Date: Aug. 16, 2018

(65) Prior Publication Data
US 2020/0024244 A1    Jan. 23, 2020

(30) Foreign Application Priority Data
Feb. 10, 2017 (EP) .................................. 17155516

(51) Int. Cl.
*C07D 307/33* (2006.01)

(52) U.S. Cl.
CPC ................................. *C07D 307/33* (2013.01)

(58) Field of Classification Search
None
See application file for complete search history.

(56) References Cited

U.S. PATENT DOCUMENTS

| 2,472,168 A | 6/1949 | Mehltretter et al. |
| 5,599,977 A | 2/1997 | Kiely et al. |
| 6,049,004 A | 4/2000 | Kiely et al. |
| 6,498,269 B1 | 12/2002 | Merbouh et al. |
| 8,669,397 B2 | 3/2014 | Boussie et al. |
| 2018/0244613 A1 | 8/2018 | Rüdenauer et al. |

FOREIGN PATENT DOCUMENTS

WO    2016131672 A1    8/2016

OTHER PUBLICATIONS

Chen, et al., "Synthesis of Stereoregular Head,Tail Hydroxylated Nylons Derived from d-Glucose", Journal of Organic Chemistry, vol. 61, Issue 17, 1996, pp. 5847-5851.
Davey, et al., "Esterification of Select Polyols with d-glucaric Acid as Model Reactions for Esterification of Starch", Carbohydrate Research, vol. 341, Issue 16, Nov. 27, 2006, pp. 2688-2693.
European Search Report for EP Patent Application No. 17155516.2, dated Apr. 7, 2017, 2 pages.
Gehret, et al.,"Convenient Large-Scale Synthesis of d-Glucaro-1,4:6,3-dilactone", The Journal of Organic Chemistry, vol. 74, Issue 21, 2009, pp. 8373-8376.
International Search Report for International Application No. PCT/EP2018/053019, dated Apr. 17, 2018, 3 pages.

*Primary Examiner* — Zinna Northington Davis
(74) *Attorney, Agent, or Firm* — Armstrong Teasdale LLP

(57) ABSTRACT

A process for preparing D-glucaro-6,3-lactone from a salt of D-glucaric acid is provided. The process includes: adding a mineral acid to a pre-cooled solution including a salt of D-glucaric acid, water, and acetone to obtain a crude mixture; allowing the crude mixture to rise to a temperature in a range of ≥15° C. to ≤35° C. and stirring the crude mixture; filtrating the crude mixture and washing with an acetone and water solvent mixture to obtain a filtrate; concentrating the filtrate under vacuum pressure to obtain a concentrated filtrate having a water content in a range of ≥20.0 wt. % to ≤40.0 wt. %, relative to an overall weight of the concentrated filtrate; storing the concentrated filtrate at a temperature in a range of ≥0° C. to ≤5° C., and optionally repeating the concentrating and storing steps to obtain a precipitate comprising D-glucaro-6,3-lactone.

14 Claims, No Drawings

PROCESS FOR PREPARING D-GLUCARO-6,3-LACTONE

CROSS-REFERENCE TO RELATED APPLICATIONS

This application is a U.S. National Phase Application of PCT/EP2018/053019, filed Feb. 7, 2018, which claims the benefit of priority to EP Application No. 17155516.2, filed Feb. 10, 2017, the contents of which are hereby expressly incorporated by reference in their entirety.

The presently claimed invention is directed to a process for preparing D-glucaro-6,3-lactone from a salt of D-glucaric acid.

BACKGROUND OF THE INVENTION

D-glucaric acid or saccharic acid is being widely used for preparing adipic acid by deoxydehydra-tion reaction. In turn, adipic acid is extensively used for manufacturing nylon-6,6. The glucaric acid is commercially available, but only as an aqueous solution. This limits the reaction solvent to water or aqueous mixtures. Alternatively, salts of D-glucaric acid have also been used for manufacturing adipic acid, to meet the growing demand. However, upon manufacturing adipic acid in the presence of the salts of D-glucaric acid, several intermediates are formed, which are difficult to separate out due to their tendency to exist as a mixture. Nevertheless, these intermediates, if obtained selectively, may turn out to be reactants for important industrial chemicals.

These important intermediates are lactones, which exist in the mono- and di-form. Examples of such mono-lactones include D-glucaro-1,4-lactone and D-glucaro-6,3-lactone while D-glucaro-1,4:6,3-lactone is one such intermediate di-lactone. Along with these mono- and di-lactones, glucaric acid is also formed which exists as an equilibrium solution with the lactones.

Of the above mentioned lactones, D-glucaro-6,3-lactone is an industrially important mono-lactone of D-glucaric acid. The commercial availability of D-glucaro-6,3-lactone is very limited or almost nil. The ability of this particular mono-lactone to be used for manufacturing various amino acids, amino esters and amino alcohols, has led to developments in arriving at various means for its selective production.

Acidification of calcium D-glucarate tetrahydrate with sulfuric acid in the presence of acetone-water is discussed by Troy et. al. [J. Org. Chem. 2009, 74, 8373-8376]. The acidification step is followed by filtration, reduced pressure operation and concentration steps to finally obtain a concentrated aqueous solution containing solid particles of a mixture of D-glucaric acid, D-glucaro-1,4-lactone, D-glucaro-6,3-lactone and D-glucaro-1,4:6,3-lactone in a fixed ratio.

Another study reported by Davey et. al. [Carbohydrate Research, 341 (2006), 2688-2693] discloses a mixture of D-glucaric acid lactones from a suspension of monopotassium glucarate in de-ionized water. During the synthesis, ion exchange resin was added, the filtrate was evaporated under reduced pressure and freeze dried to yield an amorphous solid containing a mixture of acyclic d-glucaric acid, D-glucaro-1,4-lactone, D-glucaro-6,3-lactone and D-glucaro-1,4:6,3-lactone in a fixed ratio.

Cation exchange resin was added to a mixture of monopotassium D-glucarate and water in a study conducted by Chen and Kiely [J. Org. Chem. 1996, 61, 5847-5851]. Acid form of cation exchange resin was added further with filtration and concentration carried thereafter. D-glucaro-6,3-lactone was obtained after 2-3 days of crystallization in the form of white solids and used for synthesis of head, tail hydroxylated nylons.

The existing techniques for selectively obtaining D-glucaro-6,3-lactone are not satisfactory in terms of low yield, purity of final product and time taken to obtain the final product through various process steps. Moreover, the relatively high yield and selectivity of undesirable products such as other mono- and di-lactones renders these techniques unfavorable. The requirement of high overall process temperature further renders these technique complex and uneconomical.

Thus, it was an objective of the presently claimed invention to provide a process for selectively preparing D-glucaro-6,3-lactone having high purity with process conditions which render the invention economical by optimizing them in a manner that the yield of D-glucaro-6,3-lactone is selectively maximized with minimum formation of other mono- and di-lactones as well as acid.

SUMMARY OF THE INVENTION

Surprisingly, it has been found that the ratio of mineral acid to salt of glucaric acid in the range of $\geq 1.2$ to $\leq 3.5$ in the conversion step A), acetone to water ratio in the range of $\geq 80:20$ to $\leq 98:2$ by volume in the washing step C) and the moisture content in the range of $\geq 20.0$ wt. % to $\leq 40.0$ wt. % in the concentrated filtrate in the precipitation step G), result in an overall economical and high yielding process for the production of D-glucaro-6,3-lactone. The optimized conditions of the present invention provide a selective process for preparing D-glucaro-6,3-lactone, with minimum formation of other mono- and di-lactones as well as acid.

Accordingly, in one embodiment, the presently claimed invention is directed to a process for preparing D-glucaro-6,3-lactone, comprising the steps of:

A) adding a mineral acid to a pre-cooled solution comprising a salt of D-glucaric acid, water and acetone having a temperature in the range of $\geq -10°$ C. to $\leq 5°$ C. to obtain a crude mixture, wherein the molar ratio of the mineral acid to the salt of D-glucaric acid is in the range of $\geq 1.2$ to $\leq 3.5$, B) allowing the crude mixture of step A) to rise to a temperature in the range of $\geq 15°$ C. to $\leq 35°$ C. and stirring the crude mixture, C) filtrating the crude mixture of step B) and washing with a solvent mixture comprising acetone to water in a ratio in the range of $\geq 80:20$ to $\leq 98:2$ by volume to obtain a filtrate, D) concentrating the filtrate under vacuum pressure in the range of $\geq 10$ mbar to $\leq 300$ mbar and at a temperature in the range of $\geq 20°$ C. to $\leq 40°$ C. to obtain a concentrated filtrate having a water content in the range of $\geq 20.0$ wt. % to $\leq 40.0$ wt. %, related to the overall weight of the concentrated filtrate, E) storing the concentrated filtrate at a temperature in the range of $\geq 0°$ C. to $\leq 5°$ C., F) optionally repeating steps D) and E), G) obtaining a precipitate comprising D-glucaro-6,3-lactone from the filtrate of step E) or optionally step F).

In another embodiment of the presently claimed invention, the above process is characterized in that the process further comprises the steps of:

H) washing the precipitate obtained in step G) to obtain a purified precipitate, I) filtrating and drying the purified precipitate of step H).

In another embodiment of the presently claimed invention, the above process is characterized in that the mineral acid is selected from a group consisting of sulfuric acid, hydrochloric acid, phosphoric acid and nitric acid.

In another embodiment of the presently claimed invention, the above process is characterized in that the mineral acid is sulfuric acid.

In another embodiment of the presently claimed invention, the above process is characterized in that the salt of D-glucaric acid is selected from the group consisting of calcium D-glucarate, potassium D-glucarate, sodium D-glucarate and magnesium D-glucarate.

In another embodiment of the presently claimed invention, the above process is characterized in that in step A) the pre-cooled solution is obtained by:
  a) mixing a salt of D-glucaric acid with acetone at a temperature in the range of ≥15° C. to ≤35° C.,
  b) adding water to the mixture obtained in step a),
  c) cooling the mixture obtained in step b) to a temperature in the range of ≥−10° C. to ≤5° C. to obtain a pre-cooled solution.

In another embodiment of the presently claimed invention, the above process is characterized in that in step A) the weight by volume ratio of the salt of D-glucaric acid to acetone is in the range of 1:2 to 1:5.

In another embodiment of the presently claimed invention, the above process is characterized in that in step A) the weight ratio of the salt of D-glucaric acid to water is in the range of ≥2:1 to ≤15:1.

In another embodiment of the presently claimed invention, the above process is characterized in that in step B) the crude mixture is stirred for a period in the range of ≥1 h to ≤24 h.

In another embodiment of the presently claimed invention, the above process is characterized in that in step D) and step E), independently of one another, a period in the range of ≥1 h to ≤55 h is provided.

In another embodiment of the presently claimed invention, the above process is characterized in that the step F) is performed at least once.

In another embodiment of the presently claimed invention, the above process is characterized in that in step G) the water content of the concentrated filtrate is in the range of ≥25.0 wt. % to ≤40.0 wt. %.

In another embodiment of the presently claimed invention, the above process is characterized in that in step H) washing is performed with at least one co-solvent selected from a group consisting of heptane, isopropyl alcohol, ethanol, methanol, acetonitrile, ethyl acetate, dioxane, tetrahydrofuran, methyl tert-butyl ether and a mixture thereof.

In another embodiment of the presently claimed invention, the above process is characterized in that the at least one co-solvent is a mixture of methyl tert-butyl ether and ethanol in a ratio in the range of ≥80:20 to ≤95:5 by volume.

DETAILED DESCRIPTION OF THE INVENTION

Oxidation of aldoses, for instance, with bromine-water affects only the aldehyde group, converting it into a carboxyl group. By the term "aldose", it is referred to a monosaccharide containing only one aldehyde group per molecule. The oxidation products are called aldonic acids, for example D-gluconic acid is obtained from D-glucose. When aldoses are oxidized more strongly, for example with concentrated nitric acid, then the primary alcohol group as well as the aldehyde group are transformed into carboxyl groups. The products are polyhydroxydicarboxylic acids known as aldaric acids.

An example of aldaric acid is the aldaric acid derived from glucose i.e. D-glucaric acid, also known as saccharic acid. Conventional techniques may be employed for obtaining D-glucaric acid. Such techniques are known to a person skilled in the art. Nevertheless, U.S. Pat. No. 2,472,168 illustrates a method for the preparation of D-glucaric acid from glucose using a platinum catalyst in the presence of oxygen and a base. Other oxidation methods, as disclosed in U.S. Pat. Nos. 6,049,004, 5,599,977, 6,498,269 and 8,669,397, may also be employed.

In an embodiment of the present invention, a pre-cooled solution is first prepared which comprises of a salt of D-glucaric acid, water and acetone. The salts of D-glucaric acid or saccharic acid may also be referred to as saccharates or glucarates. These salts may be obtained by any process known to a person skilled in the art and their selection for application in the present invention is not limited to any such process. In fact, these salts are abundantly available in the market.

The salts of D-glucaric acid may be preferably selected from a group consisting of calcium D-glucarate, potassium D-glucarate, sodium D-glucarate and magnesium D-glucarate. More preferably the salts are selected from the group consisting of calcium D-glucarate, potassium D-glucarate and magnesium D-glucarate. Most preferably the salts are selected from calcium D-glucarate or potassium D-glucarate. In an embodiment, the salt of D-glucaric acid is calcium D-glucarate. The salts of D-glucaric acid can be used in the form of their hydrates such as for example calcium D-glucarate tetrahydrate.

The salt of D-glucaric acid is mixed with acetone in a weight by volume ratio of the salt of D-glucaric acid: acetone, preferably in the range of ≥1:2 to ≤1:5 in step A), which is also referred to as conversion step. Most preferably the weight by volume ratio of the salt of D-glucaric acid to acetone is in the range of ≥1:2 to ≤1:4. In an embodiment, the weight by volume ratio of the salt of D-glucaric acid to acetone is in the range of ≥1:2 to ≤1:3.

The mixture comprising the salt of D-glucaric acid and acetone is agitated by mechanical means attached overhead to an equipment containing the mixture. Such techniques for agitation by mechanical means are known to a person skilled in the art. However, such mechanical means may be, such as but not limited to, a stirrer.

Water is added to the mixture obtained hereinabove and cooled to a temperature in the range of ≥−10° C. to ≤5° C. to obtain the pre-cooled solution. Preferably the weight ratio of the salt of D-glucaric acid to water is in the range of ≥2:1 to ≤15:1. More preferably the weight ratio is in the range of ≥2:1 to ≤14:1. Most preferably the weight ratio is in the range of ≥2:1 to ≤13:1. In an embodiment, the weight ratio of the salt of D-glucaric acid to water is in the range of ≥2:1 to ≤12:1.

Mineral acid is added to the pre-cooled solution while the temperature is maintained in the range of ≥−10° C. to ≤5° C. to obtain a crude mixture. The temperature of the crude mixture is maintained preferably in the range of ≥−9° C. to ≤3° C. More preferably the temperature is maintained in the range of ≥−8° C. to ≤0° C. Most preferably the temperature is maintained in the range of ≥−7° C. to ≤−2° C. In an embodiment, the temperature of the crude mixture is maintained in the range of ≥−6° C. to ≤−3° C.

By the term "mineral acid", as used hereinabove, it is referred to an acid derived from one or more inorganic acid.

These mineral acids form hydrogen ions and the conjugate base ions when dis-solved in water. Preferably, such mineral acids may be selected from a group consisting of sulfuric acid, hydrochloric acid, nitric acid and phosphoric acid. More preferably the mineral acid may be selected from a group consisting of sulfuric acid, hydrochloric acid and phosphoric acid. Most preferably the mineral acid may be sulfuric acid or phosphoric acid. In an embodiment of the present invention, the mineral acid is a sulfuric acid.

The molar ratio of mineral acid to the salt of D-glucaric acid is one of the determining factors for obtaining the desired product i.e. D-glucaro-6,3-lactone. Preferably, the molar ratio of mineral acid to the salt of D-glucaric acid is maintained in the range of ≥1.2 to ≤3.5. More preferably the molar ratio is in the range of ≥1.2 to ≤2.5. Most preferably the molar ratio is in the range of ≥1.2 to ≤2.0. In an embodiment, the molar ratio of mineral acid to the salt of D-glucaric acid is in the range of ≥1.2 to ≤1.8.

The addition of mineral acid results in an acidification reaction. By the term "acidification reaction", it is referred to the reaction between the mineral acid and the salt of D-glucaric acid of the pre-cooled solution. Favourable reaction conditions are maintained by maintaining the temperature in the range of ≥−10° C. to ≤5° C. Preferably the temperature is maintained in the range of ≥−8° C. to ≤5° C. More preferably the temperature is maintained in the range of ≥−8° C. to ≤3° C. Most preferably the temperature is maintained in the ≥−7° C. to ≤1° C. In an embodiment, the temperature is maintained in the range of ≥−5° C. to ≤0° C.

The reaction products obtained as a result of this acidification reaction are referred to as the crude mixture. Typically, the crude mixture comprises of an equilibrium solution of lactones and acid. By the term "equilibrium", it is referred to the solution obtained as a result of the acidification reaction and the concentration of which is not affected with time. The lactones may be mono-lactones and di-lactones. In an embodiment, mono-lactones such as D-glucaro-1,4-lactone and D-glucaro-6,3-lactone are obtained. D-glucaro-1,4:6,3-lactone as a di-lactone and D-glucaric acid are also obtained in the equilibrium solution. The yield % ratio of D-glucaro-1,4-lactone:D-glucaro-6,3-lactone:D-glucaro-1,4:6,3-lactone:D-glucaric acid is generally 30%:30%:37%:3%, respec-tively.

The temperature of the crude mixture comprising an equilibrium solution of mono- and di-lactones along with D-glucaric acid is allowed to rise gradually in the range of ≥15° C. to ≤35° C. with constant stirring according to step B). Preferably the temperature of the crude mixture is allowed to rise in the range of ≥15° C. to ≤30° C. More preferably the temperature is allowed to rise in the range of ≥20° C. to ≤30° C. Most preferably the temperature is allowed to rise in the range of ≥22° C. to ≤27° C. In an embodiment, the temperature of the crude mixture is allowed to rise in the range of ≥23° C. to ≤25° C. under constant stirring.

The time period during which the temperature of the crude mixture is allowed to rise gradually and stirred continuously thereafter is in the range of ≥1 h to ≤24 h. Preferably, the period is in the range of ≥2 h to ≤22 h, more preferably in the range of ≥2 h to ≤21 h. Most preferably in the range of ≥2 h to ≤20 h.

In order to selectively precipitate D-glucaro-6,3-lactone from the equilibrium solution, filtration of the crude mixture is carried out according to step C) using any suitable filter media known to a person skilled in the art, such as but not limited to, Whatman filter paper of grade-I and/or Celite® 545. Although, a substantial portion of the crude mixture passes through the filter paper, however, some amount of the crude mixture along with other un-reacted impurity remains as a residue on the filter media in the form of a cake. Particularly, in order to increase the yield of D-glucaro-6,3-lactone, the cake is washed with a solvent mixture comprising acetone and water.

The solvent mixture may be used in excess of the residue. Preferably the ratio of solvent and salt of D-glucaric acid may be in the range of ≥1:1 to ≤10:1 volume by weight. More preferably the ratio may be in the range of ≥2:1 to ≤8:1 volume by weight. Most preferably the ratio may be in the range of ≥2:1 to ≤5:1 volume by weight. In an embodiment, the ratio of solvent and salt of D-glucaric acid may be in the range of ≥2:1 to ≤4:1 volume by weight.

The yield of the desired mono-lactone i.e. D-glucaro-6,3-lactone, is increased by washing the residue left over the filter media with a solvent mixture. The solvent mixture comprises of acetone and water in a ratio in the range of ≥80:20 to ≤98:2 by volume to finally obtain a filtrate solution. Preferably the solvent mixture comprises of acetone and water in a ratio in the range of ≥80:20 to ≤96:4 by volume. More preferably the ratio is in the range of ≥83:17 to ≤96:4 by volume. Most preferably the ratio is in the range of ≥85:15 to ≤95:5 by volume.

The filtrate obtained upon washing the residue still comprises of D-glucaro-1,4-lactone, D-glu-caro-1,4:6,3-lactone and D-glucaric acid, however, the amount of the desired mono-lactone i.e. D-glucaro-6,3-lactone is enhanced. The amount of water or moisture in the filtrate solution is an important factor which decides the yield of a particular mono- or di-lactone and the acid. A slight variation in the water content may result in an increase or decrease of the desired mono-lactone. Therefore, it is essential to concentrate the filtrate to achieve the increased yield of D-glucaro-6,3-lactone.

The concentration step, i.e. the step D), is performed under vacuum conditions and a concentrated filtrate is obtained. Typically, the concentrated filtrate comprises of a mixture of D-glucaro-1,4-lactone, D-glucaro-1,4:6,3-lactone, D-glucaro-6,3-lactone and D-glucaric acid, but with increased yield of the desired mono-lactone. By the term "vacuum conditions", it is referred to sub-atmospheric conditions of pressure.

Concentration of the filtrate may be performed by means of any suitable equipment known to a person skilled in the art which operate under vacuum conditions. However, a typical rotary evaporator may be used for carrying out the concentration step. The choice of a particular rotary evaporator should be made based on the desired conditions of temperature and pressure, as described hereinbelow.

The water content or moisture content in the concentrated filtrate affects the precipitation of the desired monolactone i.e. D-glucaro-6,3-lactone. One of the main parameters affecting the moisture content of the filtrate is pressure. Concentration of the mixture is performed by evaporation which is carried out at reduced pressures, preferably under vacuum conditions. The vacuum pressure is maintained in the range of ≥10 mbar to ≤300 mbar. Preferably the vacuum pressure is in the range of ≥20 mbar to ≤280 mbar. More preferably the vacuum pressure is in the range of ≥40 mbar to ≤260 mbar. Most preferably the vacuum pressure is in the range of ≥50 mbar to ≤250 mbar.

Another important parameter for controlling the moisture content in the filtrate is temperature. The filtrate is concentrated under vacuum pressure and at temperature in the range of ≥20° C. to ≤40° C. Preferably the temperature is in the range of ≥20° C. to ≤35° C. More preferably the temperature is in the range of ≥25° C. to ≤35° C. Most preferably the temperature is in the range of ≥27° C. to ≤33° C.

Apart from temperature and pressure, the duration of concentration step is another parameter which controls the moisture content of the concentrated filtrate. Typically, a duration in the range of ≥1 h to ≤55 h is provided during the concentration step. Preferably the duration is in the range of ≥2 h to ≤45 h. More preferably the duration is in the range of ≥3 h to ≤35 h. Most preferably the duration is in the range of ≥4 h to ≤25 h. In an embodiment, duration of the concentration step is in the range of ≥5 h to ≤20 h.

The concentrated filtrate obtained as a result of the concentration step is stored in atmospheric pressure and temperature for a certain duration to allow precipitation of D-glucaro-6,3-lactone to occur. This step may be hereinafter referred to as storage step, i.e. step E) is referred to as the storage step.

The temperature prevailing in the storing step is preferably in the range of ≥0° C. to ≤5° C. More preferably the temperature is in the range of ≥1° C. to ≤5° C. Most preferably the temperature is in the range of ≥1° C. to ≤4° C. In an embodiment, the temperature in the range of ≥2° C. to ≤4° C. is maintained.

Typically, the duration for storing the concentrated filtrate is in the range of ≥1 h to ≤55 h. More preferably the concentrated filtrate is stored for a period in the range ≥3 h to ≤45 h. Most preferably the period is in the range of ≥3 h to ≤35 h. In an embodiment, the concentrated filtrate is stored for a period in the range of ≥5 h to ≤25 h.

The storage step does not substantially alter the moisture content of the concentrated filtrate. During the storage of the concentrated filtrate, selective precipitation of only D-glucaro-6,3-lactone occurs as white solid occurs, while other mono-lactone, di-lactone and acid do not precipitate.

The moisture content of the concentrated filtrate is measured using any of the techniques known to a person skilled in the art, such as but not limited to, Karl Fischer titration method. Preferably the moisture content desired for selectively obtaining D-glucaro-6,3-lactone precipitate should be in the range of ≥20.0 wt. % to ≤40.0 wt. % related to the overall weight of the concentrated filtrate. The importance of moisture content in the concentrated filtrate may be understood by the fact that the moisture content of less than 20.0 wt. % results in formation of other mono- and di-lactone along with the acid, but does not result in any D-glucaro-6,3-lactone. On the other hand, a moisture content beyond 40.0 wt. % may result in some precipitation of D-glucaro-6,3-lactone, but the time required is much higher than that described hereinabove.

Therefore, to achieve high yields of D-glucaro-6,3-lactone, the moisture content is kept in the range of ≥20.0 wt. % to ≤40.0 wt. %, related to the overall weight of the concentrated filtrate. In an embodiment, the moisture content in the concentrated filtrate is kept in the range of ≥25.0 wt. % to ≤40.0 wt. %, related to the overall weight of the concentrated filtrate.

In order to do so, the present invention optionally requires the concentration and storage steps to be repeated until the moisture content of the concentrated filtrate is in the range of ≥20.0 wt. % to ≤40.0 wt. %, related to the overall weight of the concentrated filtrate. The concentrated filtrate obtained after performing the storage step for the first time is now utilized for further and subse-quent repetitions of the concentration and storage steps.

If the moisture content of the concentrated filtrate is not in the range, as described hereinabove, the concentration and storage steps are repeated. The concentrated filtrate may be further subjected to concentration and storage step until the moisture content is in the range as prescribed in the present invention and high yields of D-glucaro-6,3-lactone obtained subsequently.

The concentration and storage steps when repeated with the concentrated filtrate, result in partial precipitation of D-glucaro-6,3-lactone with the moisture content in the range as described hereinabove. By the term 'partial precipitation', it is referred to the incomplete precipitation of D-glu-caro-6,3-lactone in the concentrated filtrate obtained after the concentration and storage step. The concentrated filtrate obtained after partial precipitation may still contain some amount of the desired mono-lactone, which may be further precipitated during complete precipitation. Typically, the partial precipitate comprises of precipitate of D-glucaro-6,3-lactone along with D-glucaro-1,4-lactone, D-glucaro-1,4:6,3-lactone and D-glucaric acid.

Complete precipitation of the concentrated filtrate further increases the yield of the desired mono-lactone. Therefore, in order to achieve the complete precipitation of D-glucaro-6,3-lactone, the partially precipitated mixture of D-glucaro-6,3-lactone obtained hereinabove is used for further repeating the concentration and storage steps, in the manner as described hereinabove with the amount of moisture content being checked every time.

The number of repetitions of the concentration and storage steps may be determined based on the moisture content and yield of the desired mono-lactone i.e. D-glucaro-6,3-lactone. Nevertheless, the concentration and storage steps may be repeated at least once or twice or thrice. In an embodiment, the concentration and storage steps may be repeated at least once. If the concentration and storage steps are repeated once, the following temporal sequence of steps applies A)→B)→C)→D)→E)→D)→E)→(G). If the concentration and storage steps are repeated twice, the following temporal sequence of steps applies A)→B)→C)→D) →E)→D)→E)→D)→E)→(G).

During the selective precipitation of the desired mono-lactone in a series of concentration and storage steps, some amount of the desired mono-lactone may be lost. However, the loss of the desired mono-lactone along with other constituents of the filtrate or concentrated filtrate is in minor amounts, which may be difficult to recover. Although, if the lost mono-lactone is recovered, the overall yield of the final precipitate will increase, but the overall cost of recovering might render the process uneconomical. Nevertheless, the lost mono-lactone may be recovered using techniques known to a person skilled in the art, such as but not limited to, distillation.

In a preferred embodiment of the presently claimed invention, a process for preparing D-glucaro-6,3-lactone is disclosed, said process comprising the steps of:

A) adding sulfuric acid to a pre-cooled solution comprising calcium D-saccharate, water and acetone having a temperature in the range of ≥−10° C. to ≤5° C. to obtain a crude mixture, wherein the molar ratio of the sulfuric acid to the calcium D-saccharate is in the range of ≥1.2 to ≤1.8, B) allowing the crude mixture of step A) to rise to a temperature in the range of ≥15° C. to ≤35° C. and stirring the crude mixture, C) filtrating the crude mixture of step B) and washing with a solvent mixture comprising acetone to water in a ratio in the range of ≥85:15 to ≤95:5 by volume to obtain a filtrate, D) concentrating the filtrate under vacuum pressure in the range of ≥10 mbar to ≤300 mbar and at a temperature in the range of ≥20° C. to ≤40° C. to obtain a concentrated filtrate having a water content in the range of ≥20.0 wt. % to ≤40.0 wt. %, related to the overall weight of the concentrated filtrate, E) storing the concentrated filtrate at a temperature in the range of ≥0° C. to ≤5° C., F) optionally repeating steps D) and E), G) obtaining a precipitate comprising D-glucaro-6,3-lactone from the filtrate of step E) or optionally step F).

The precipitate obtained after performing the concentration and storage steps, as described hereinabove, can be washed once again to obtain a purified precipitate comprising D-glucaro-6,3-lactone. This step, i.e. the purification step, increases the purity of D-glucaro-6,3-lactone by washing the precipitate with at least one co-solvent.

The at least one co-solvent may be used in excess of the precipitate. Preferably the ratio of the at least one co-solvent and salt of D-glucaric acid may be in the range of ≥1:1 to ≤15:1 volume by weight. More preferably the ratio may be in the range of ≥2:1 to ≤13:1 volume by weight. Most preferably the ratio may be in the range of 2:1 to ≤10:1 volume by weight. In an embodiment, the ratio of at least one co-solvent and salt of D-glucaric acid may be in the range of ≥2:1 to ≤8:1 volume by weight.

The at least one co-solvent may be selected from a group consisting of heptane, isopropyl alcohol, ethanol, methanol, acetonitrile, ethyl acetate, dioxane, tetrahydrofuran, methyl tert-butyl ether and a mixture thereof.

Preferably the at least one co-solvent may be selected from a group consisting of heptane, isopropyl alcohol, ethanol, ethyl acetate, dioxane, tetrahydrofuran, methyl tert-butyl ether and a mixture thereof.

More preferably the at least one co-solvent may be selected from a group consisting of ethanol, ethyl acetate, dioxane, tetrahydrofuran, methyl tert-butyl ether and a mixture thereof.

Most preferably the at least one co-solvent may be selected from a group consisting of ethanol, tetrahydrofuran, methyl tert-butyl ether and a mixture thereof.

In an embodiment the at least one co-solvent is a mixture of methyl tert-butyl ether and ethanol.

The mixture of methyl tert-butyl ether and ethanol as the co-solvent may be in a ratio in the range of ≥80:20 to ≤95:5 by volume. Preferably the ratio may be in the range of ≥82:18 to ≤95:5 by volume. More preferably the ratio may be in the range of ≥82:18 to ≤93:7 by volume. Most preferably the ratio may be in the range of ≥84:16 to ≤93:7 by volume. In an embodiment, methyl tert-butyl ether and ethanol are in a ratio in the range of ≥84:16 to ≤90:10 by volume to obtain the purified precipitate.

The purified precipitate obtained in step H) is subjected to filtration and a filtration product is obtained thereby, which comprises of high purity D-glucaro-6,3-lactone precipitate as white solids. Any suitable filtration technique, such as but not limited, to a Buchner funnel equipped with a Whatman filter paper of grade-I may be applied for this purpose in step I), i.e. the isolation step.

Vacuum drying of the filtration product further increases the purity of D-glucaro-6,3-lactone. For instance, the filtration product may be vacuum dried at pressure ranging between ≥50 mbar to ≤200 mbar. Purity as high as 90% for D-glucaro-6,3-lactone may be achieved. The moisture content of D-glucaro-6,3-lactone in the range of ≥25.0 wt. % to ≤40.0 wt. %, as described hereinabove, is preferably reduced to ≥1.0 wt. % to ≤10.0 wt. % as measured by Karl Fischer titration.

If the purification step and isolation step are performed, the following temporal sequence of steps applies A)→B)→C)→D)→E)→G)→H)→I). If the concentration and storage steps are repeated once and additionally the purification step and isolation step are performed, the following temporal sequence of steps applies A)→B)→C)→D)→E)→D)→E)→G)→H)→I). If the concentration and storage steps are repeated twice and additionally the purification step and isolation step are performed, the following temporal sequence of steps applies A)→B)→C)→D)→E)→)→D)→E)→D)→E)→G)→H)→I).

The process according to the presently claimed invention has several advantages over conventional techniques, e.g.
- selectively obtaining D-glucaro-6,3-lactone, and/or
- obtaining high yield and purity of D-glucaro-6,3-lactone, and/or
- low temperature and pressure conditions of the process render it economical, and/or
- ease of scaling the process to the meet huge industrial requirements, and/or
- high purity and yield of D-glucaro-6,3-lactone imparts huge downstream potential, such as but not limited to, as a raw material for various amino acids, esters and alcohols.

EXAMPLES AND COMPARATIVE EXAMPLES

| Compounds | |
|---|---|
| Salt of D-glucaric acid | Calcium D-saccharate tetrahydrate |
| Mineral acid | Sulfuric acid |
| Washing solvent | Acetone |
| Co-solvent | Methyl tert-butyl ether (MTBE) Ethanol (EtOH) |
| Filter media | Celite ® 545 |
| Hydranal ® Medium-K | |
| Hydranal ® Composite-5 | |
| are available from Sigma Aldrich | |

Process for Preparing D-glucaro-6,3-lactone

Example 1-100 g of calcium D-saccharate tetrahydrate (0.312 moles) was charged to a 500 mL, 4-neck round bottom flask containing 300 mL of acetone at a temperature of 25° C. The flask was equipped with overhead stirrer having rpm indicator and water condenser. 8.4 g of water was added and the mixture was cooled to −5° C. to obtain a pre-cooled solution. 52 g of sulfuric acid (0.52 moles) was now added to the pre-cooled solution. The temperature was maintained below 0° C. to form a crude mixture. Upon complete addition of the acid, the temperature of the crude mixture was allowed to rise gradually to 25° C. over a period of 1-2 hours and stirred at 200 rpm for 16 hours maintaining the same temperature. The crude mixture was then filtered through a bed of Celite® 545 over a 15 μm size of filtration cloth and the residue was washed thrice with the solvent mixture comprising acetone:water in a ratio of 86:14 by volume (3×70 mL) to obtain a filtrate solution. The filtrate solution was then concentrated on a rotary evaporator at 30° C. under a vacuum pressure of 50 mbar over a period of 8 h. A thick oily concentrated filtrate was obtained, which was stored in a refrigerator at 3° C. for 16 h. This resulted in partial precipitation of the compound. The partially precipitated mixture was concentrated again on rotary evaporator at 30° C. under vacuum pressure of 50 mbar for 4 h, which resulted in increase in precipitation of the solid compound. This precipitated compound was stored at 3° C. for 16 h, which resulted in complete precipitation of the desired compound i.e. D-glucaro-6,3-lactone. The precipitated compound was then washed by a co-solvent solution comprising of MTBE:EtOH in the ratio of 86:14 by volume (625 mL) at 25° C. to obtain a purified precipitate. The purified precipitate is subjected to filtration and vacuum drying to obtain D-glucaro-6,3-lactone of 95% purity and yield of 55%, based on calcium D-saccharate.

Further examples and comparative examples were conducted with process parameters of the present invention, as described hereinabove. Effect of different parameters were checked and have been reported hereinbelow.

TABLE 1

Effect of sulfuric acid concentration and moisture content

| Example | Molar ratio Sulfuric acid:Calcium D-saccharate tetrahydrate | Final moisture content of the concentrated filtrate [in wt. %] | Total time taken for partial precipitation [in h] | Total time taken for complete precipitation [in h] | % Yield |
|---|---|---|---|---|---|
| Comp. Ex. 1 | 1.00 | 52.1 | No precipitation occurred | | |
| Ex. 2 | 1.20 | 28.2 | 69 | 22 | 39 |
| Ex. 3 | 1.40 | 27.5 | 21 | 24 | 54 |
| Ex. 4 | 1.67 | 38.1 | 18 | 24 | 60 |

The abovementioned examples and comparative examples were conducted with 200 g of calcium D-saccharate tetrahydrate and an acetone:water ratio of 86:14 by volume during washing. MTBE:EtOH in the ratio of 86:14 by volume was used as co-solvent for washing the precipitate. The concentration and storage steps were repeated twice. Other procedures for obtaining the final product were similar to that of example 1. As evident, the % yield of D-glucaro-6,3-lactone increased with the amount of sulfuric acid for acidification.

Further, due to increase in moisture content of the concentrated filtrate, time taken for partial and complete precipitation increased with a substantial decrease in the yield of D-glucaro-6,3-lactone. This may be attributed to the fact that high moisture content requires more time for moisture to evaporate in the concentration step. Moreover, the molar ratio of sulfuric acid to calcium D-saccharate tetrahydrate also affects the moisture content, thereby altering the yield of D-glucaro-6,3-lactone.

In order to demonstrate the effect of acetone to water ratio during washing, experiments were conducted in a manner similar to example 1 The concentration and storage steps repeated once and the amount of co-solvent MTBE:EtOH ratio was maintained at 85:15 by volume. The result obtained are tabulated below.

TABLE 2

Effect of acetone to water ratio

| Example | Ratio by volume Acetone:water | Total time taken for partial precipitation [in h] | Total time taken for complete precipitation [in h] | % Yield |
|---|---|---|---|---|
| Ex. 5 | 86:14 | 28 | 48 | 61 |
| Ex. 6 | 95:05 | 25 | 23 | 55 |

It may be observed that an increase in the amount of moisture during washing, results in an overall increase in the yield of D-glucaro-6,3-lactone, however, an increase in the amount of time taken during the concentration and storage step also increases. This may be attributed to the fact that the amount of water used during washing results in an increase in the amount of moisture content in the concentrated filtrate, thereby increasing the precipitation time.

Example 7-200 g of calcium D-saccharate tetrahydrate (0.643 moles) was charged to a 1 L, 4-neck round bottom flask containing 600 mL of acetone at a temperature of 25° C. The flask was equipped with overhead stirrer having rpm indicator and water condenser. 16.8 g of water was added and the mixture was cooled to −5° C. to obtain a pre-cooled solution. 105 g of sulfuric acid (1.04 moles) was now added to the pre-cooled solution. The temperature was maintained below 0° C. to form a crude mixture. Upon complete addition of the acid, the temperature of the crude mixture was allowed to rise gradually to 25° C. over a period of 1-2 hours and stirred at 200 rpm for 16 hours maintaining the same temperature. The crude mixture was then filtered through a bed of Celite® 545 over a 15 μm size of filtration cloth and the residue was washed thrice with the solvent mixture comprising acetone:water in a ratio of 86:14 by volume (3×140 mL) to obtain a filtrate solution. The filtrate solution was then concentrated in a rotary evaporator at 30° C. under a vacuum pressure of 50 mbar over a period of 8 h. A thick oily concentrated filtrate was obtained, which was stored in a refrigerator at 3° C. for 16 h. This resulted in partial precipitation of the compound. The partially precipitated mixture was concentrated again on rotary evaporator at 30° C. under vacuum pressure of 50 mbar for 4 h, which resulted in increase in precipitation of the solid compound. This precipitated compound was stored at 3° C. for 3 h, which resulted in complete precipitation of the desired compound i.e. D-glucaro-6,3-lactone. The precipitated compound was then washed by a co-solvent solution comprising of MTBE:EtOH in the ratio of 88:12 by volume (1478 mL) at 25° C. to obtain a purified precipitate. The purified precipitate is subjected to filtration and vacuum drying to obtain D-glucaro-6,3-lactone of 90% purity and yield of 65%, based on calcium D-saccharate.

The invention claimed is:

1. A process for preparing D-glucaro-6,3-lactone, comprising the steps of:
   A) adding a mineral acid to a pre-cooled solution comprising a salt of D-glucaric acid, water and acetone having a temperature in a range of ≥−10° C. to ≤5° C. to obtain a crude mixture, wherein a molar ratio of the mineral acid to the salt of D-glucaric acid is in a range of ≥1.2 to ≤3.5,
   B) allowing the crude mixture of step A) to rise to a temperature in a range of ≥15° C. to ≤35° C. and stirring the crude mixture, C) filtrating the crude mixture of step B) and washing with a solvent mixture comprising acetone to water in a ratio in a range of ≥80:20 to ≤98:2 by volume to obtain a filtrate, D) concentrating the filtrate under vacuum pressure in a range of ≥10 mbar to ≤300 mbar and at a temperature in a range of ≥20° C. to ≤40° C. to obtain a concentrated filtrate having a water content in a range of ≥20.0 wt. % to ≤40.0 wt. %, related to an overall weight of the concentrated filtrate, E) storing the concentrated filtrate at a temperature in a range of ≥0° C. to ≤5° C., F) optionally repeating steps D) and E), and G) obtaining a precipitate comprising D-glucaro-6,3-lactone from the concentrated filtrate of step E) or optionally step F).

2. The process according to claim 1 further comprising the steps of:

H) washing the precipitate obtained in step G) to obtain a purified precipitate, and I) filtrating and drying the purified precipitate of step H).

3. The process according to claim 1, characterized in that the mineral acid is selected from a group consisting of sulfuric acid, hydrochloric acid, phosphoric acid and nitric acid.

4. The process according to claim 3, characterized in that the mineral acid is sulfuric acid.

5. The process according to claim 1, characterized in that the salt of D-glucaric acid is selected from the group consisting of calcium D-glucarate, potassium D-glucarate, sodium D-glucarate and magnesium D-glucarate.

6. The process according to claim 1, characterized in that in step A) the pre-cooled solution is obtained by:

a) mixing the salt of D-glucaric acid with acetone at a temperature in a range of ≥15° C. to <35° C., b) adding water to the mixture obtained in step a), and c) cooling the mixture obtained in step b) to a temperature in the range of ≥−10° C. to ≤5° C. to obtain the pre-cooled solution.

7. The process according to claim 1, characterized in that in step A) a weight by volume ratio of the salt of D-glucaric acid to acetone is in a range of ≥1:2 to ≤1:5.

8. The process according to claim 1, characterized in that in step A) a weight ratio of the salt of D-glucaric acid to water is in a range of ≥2:1 to ≤15:1.

9. The process according to claim 1, characterized in that in step B) the crude mixture is stirred for a period in a range of ≥1 h to ≤24 h.

10. The process according to claim 1, characterized in that in step D) and step E), independently of one another, a period in a range of ≥1 h to ≤55 h is provided.

11. The process according to claim 1, characterized in that step F) is performed at least once.

12. The process according to claim 1, characterized in that in step D) the water content of the concentrated filtrate is in a range of ≥25.0 wt. % to ≤40.0 wt. %.

13. The process according to claim 2, characterized in that in step H) washing is performed with at least one co-solvent selected from a group consisting of heptane, isopropyl alcohol, ethanol, methanol, acetonitrile, ethyl acetate, dioxane, tetrahydrofuran, methyl tert-butyl ether and a mixture thereof.

14. The process according to claim 13, characterized in that the at least one co-solvent is a mixture of methyl tert-butyl ether and ethanol in a ratio in a range of ≥80:20 to <95:5 by volume.

\* \* \* \* \*